United States Patent [19]

Gaiser

[11] 4,146,566
[45] Mar. 27, 1979

[54] SELF-CONTAINED VOLATILE COMPONENT DISPENSING PACKAGE

[76] Inventor: Conrad J. Gaiser, 24 S. 66th Place, Long Beach, Calif. 90803

[21] Appl. No.: 812,581

[22] Filed: Jul. 5, 1977

Related U.S. Application Data

[63] Continuation-in-part of Ser. No. 742,560, Nov. 17, 1976.

[51] Int. Cl.² .......................... A61L 9/01; A61L 9/04
[52] U.S. Cl. .................................. 422/122; 422/123; 422/306
[58] Field of Search ............... 21/123, 124, 122, 121, 21/125, 74 R

[56] References Cited

U.S. PATENT DOCUMENTS

| 476,269 | 6/1892 | Hill | 21/123 |
| 525,497 | 9/1894 | Hoffman | 21/124 |
| 712,667 | 11/1902 | Goulardt | 21/124 |
| 769,864 | 9/1904 | Hall | 21/122 |
| 896,552 | 8/1908 | Keefer | 21/124 |
| 1,540,197 | 6/1925 | Treadwell | 21/124 UX |
| 1,614,817 | 1/1927 | Andrew | 21/125 |
| 2,585,339 | 2/1952 | Miller | 21/74 R |
| 2,614,820 | 10/1952 | Boydjieff | 21/74 R UX |
| 3,967,926 | 7/1976 | Rozenfeld et al. | 21/2.5 B |

FOREIGN PATENT DOCUMENTS

1180965  6/1959  France ........................ 21/124

OTHER PUBLICATIONS

Balsam et al., Cosmetics Science and Technology, Wiley Interscience, New York, NY, pp. 339, 348 & frontispiece.

*Primary Examiner*—Barry S. Richman
*Attorney, Agent, or Firm*—Fulwider, Patton, Rieber, Lee & Utecht

[57] ABSTRACT

A dispensing package for a volatile composition such as a room deodorant and the like that comprises a container having at least two chambers. In one of the chambers is packaged a bed of inert solid, adsorbent granules having absorbed thereon a volatile ingredient for dispensing into the atmosphere. The container has an outlet vapor port in a wall of the chamber and a second vapor inlet port which communicates with a second chamber; the latter having a collapsible wall surface. A check valve is provided in the wall of the second chamber to permit air intake whereby volatile components adsorbed on the surface of the solid bed of granules can be dispensed into the atmosphere by pumping the collapsible wall of the second chamber, thereby forcing air through the bed of solid granules and desorbing of the the volatile adsorbate, which is dispensed into the atmosphere. Preferably, the bed of solid adsorbent is formed with a plurality of volatile components of different volatilities which are each adsorbed onto an inert carrier to provide a plurality of volatile-component-bearing, solid fractions which are blended together in preselected proportions to provide the desired proportional release rate of each of the volatile components.

12 Claims, 11 Drawing Figures

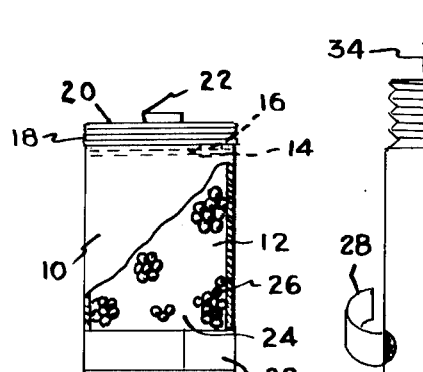
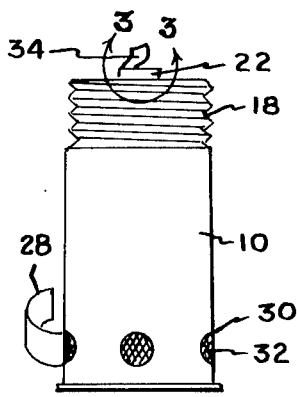
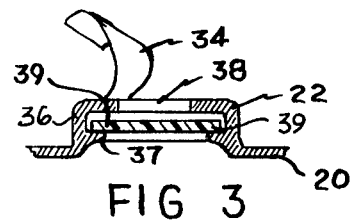
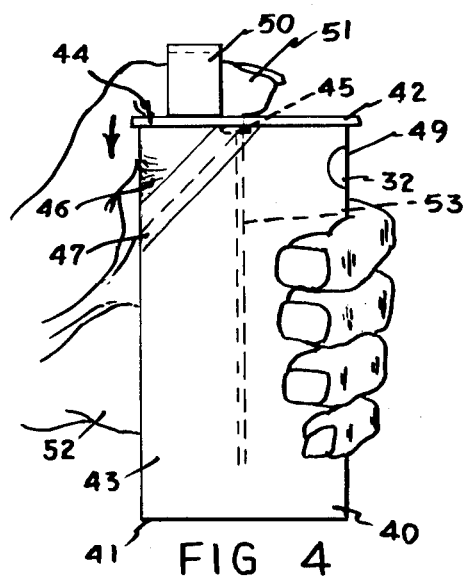
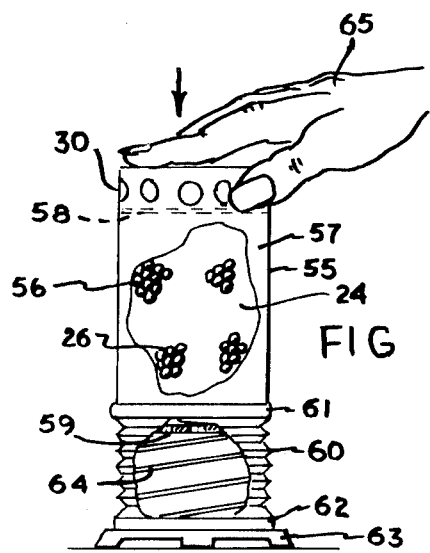
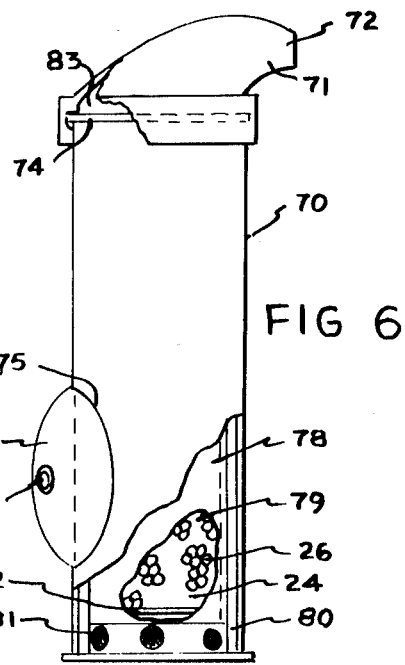
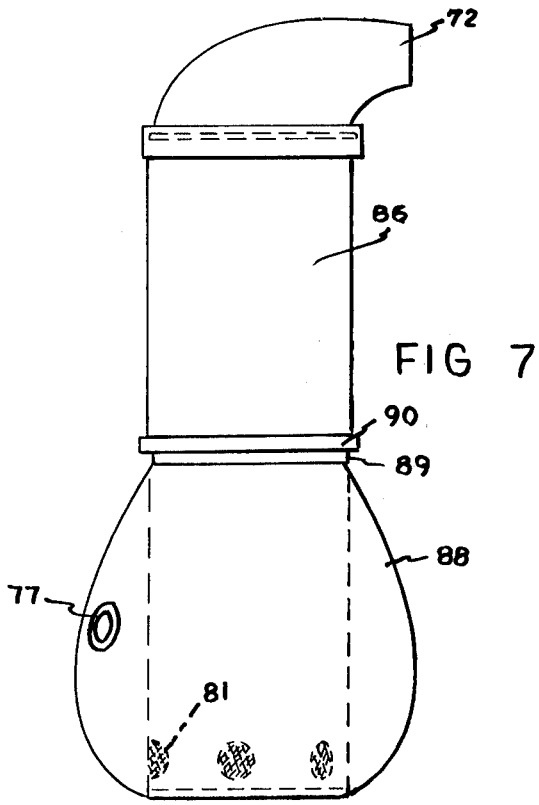

SELF-CONTAINED VOLATILE COMPONENT DISPENSING PACKAGE

REFERENCE TO RELATED APPLICATIONS

This application is a continuation-in-part of our co-pending application Ser. No. 742,560, filed Nov. 17, 1976.

BACKGROUND OF THE INVENTION

1. Field of Invention

This invention relates to a volatile dispensing package which provides for forced air circulation through a bed of solid adsorbent to effect desorption of a volatile adsorbate such as a perfume and the like for a room deodorant.

2. Brief Statement of the Prior Art

Compositions such as room deodorants and the like comprise a volatile perfume agent in a liquid solution or a gel cake. As the product evaporates, the concentration of the volatile agent or size of the solid cake steadily decreases, resulting in a steadily decreasing release rate of the volatile perfume agent. Deodorants also are frequently formed with a plurality of volatile ingredients, e.g., the perfumes and odor masking agents may be a blend of several perfumes, agents and various solvents, or other ingredients of different volatilities employed in the composition. Evaporation from these deodorants also causes changes in the deodorant composition, changing the amount and composition of the released vapor.

The deodorant compositions are employed in a variety of vapor-releasing forms. Some of the deodorants are consolidated into a cake or solid composite, frequently using a deliquescent or sublimating material such as napthalene, paradichlorobenzene, soap, and the like. The solid cake is placed in a container having a closure member which can be removed or positioned to release the active agents. Liquid deodorant compositions are employed with wicks and the like to provide a surface for releasing the volatile ingredients, the user controlling the release rate by the extent of exposure of the wick of the package.

The aforedescribed deodorant products have a number of disadvantages, e.g., the products do not have any provision for a forced air circulation through or about the vapor releasing element such as the wick of a liquid deodorant composition or a solid cake or composite. Solid deodorants unavoidably shrink during their life and have a steadily decreasing release rate proportional to their steadily decreasing surface area. Liquids exhibit a similar declining release rate resulting from a decreasing concentration of the volatile component in the liquid. Since deodorant compositions are frequently formed of a plurality of volatile components having different relative volatility, these compositions unavoidably change during use resulting in a continuing change in the composition of the released volatile components.

Deodorants are also packaged in aerosol, pressure containers with a liquid, vaporizable propellent such as a fluorochloro hydrocarbon and the like. These packages have the disadvantage of relatively low net contents of useful deodorant and additionally, are finding public disfavor because of the possibility of adverse environmental effects of the propellent.

It is, therefore, desirable to provide a deodorant composition which can be provided in a package having means for forced air circulation through the package to effect a controlled dispensing of the volatile components. It is also desirable that the deodorant be packaged to insure that the deodorant will maintain a substantially constant composition of the released volatile ingredients throughout its useful life.

This invention comprises a package for the dispensing of a volatile component which comprises a container having vapor inlet and outlet port means communicating with an internal, first chamber, and a collapsible, second chamber mounted in sealing communication with the first chamber through its vapor inlet port means. The collapsible second chamber communicates exteriorly through a check valve means mounted in a wall of the chamber whereby the collapsible second chamber can function as an air pump for introducing a flow of air through the first chamber. The first chamber is substantially filled with a bed of inert solid adsorbent granules which contain adsorbed thereon an adsorbate formed of at least one volatile ingredient for dispensing to the atmosphere through the vapor outlet port means.

The solid adsorbent and the volatile ingredient adsorbate are selected to provide an adsorption isotherm characteristic of substantially constant vapor pressure, and independent of the concentration of the adsorbate on the solid adsorbent. In the preferred embodiment, the bed of inert solid adsorbent granules comprises an admixture of a plurality of inert solid fractions, each fraction comprising an inert, particulate, solid carrier having adsorbed thereon a volatile ingredient of a volatile composition to provide volatile, component-bearing solid fractions of preselected specific surface area, adsorbate concentration, particle size and adsorption isotherm characteristics. The solid fractions are blended together in proportions to provide a proportional release rate of their respective volatile component whereby the vapor released from the package is of a preselected, desired composition.

BRIEF DESCRIPTION OF THE DRAWINGS

The invention will be described with reference to the drawings of which:

FIGS. 1–3 illustrate a package of the invention;

FIG. 4 illustrates an alternative package of the invention;

FIG. 5 illustrates an alternative package of the invention;

FIG. 6 illustrates another embodiment of the invention;

FIG. 7 illustrates an alternative embodiment of the invention.

DESCRIPTION OF PREFERRED EMBODIMENTS

Figure 8:
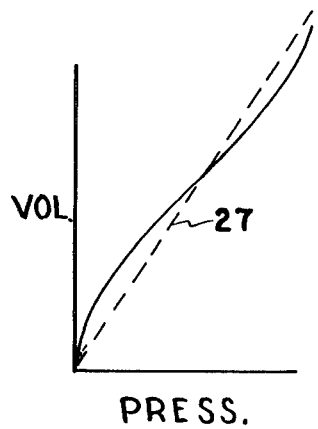
FIGS. 8–10 illustrate typical adsorption isotherms of volatile components on adsorbents.

Referring now to FIG. 1, there is illustrated a package of the invention in a form intended for distribution and marketing to the consumer. As there illustrated, the package comprises a container 10 formed with a first, internal chamber 12 which has an end wall 14 having an aperture or port means 16 that communicates with a second chamber formed by a collapsible side wall 18 of a bellows construction and an end wall 20. The end wall 20 has a check valve means 22 to permit air flow into the collapsible chamber defined by bellows side wall 18 and end wall 20. Packed within the first internal chamber 12 is a bed of 24 of inert solid adsorbent granules 26 which contain an adsorbate of a volatile ingredient for dispensing into the atmosphere through the vapor outlet port means of the first container.

The vapor outlet port means of the first chamber 12 of container 10 can be temporarily shielded or covered by suitable means such as an adhesive tear tape 28 and the like.

Referring now to FIG. 2, the tear tape 28 is shown being removed from the container 10, exposing the vapor outlet port means which are in the form of a plurality of apertures 30 which can be covered by a perforated shield such as a screen 32 and the like. The check valve means 22 is preferably also covered by a sealing membrane such as a tear tape 34 and the like. The user can remove this tear tape and permit the air pump means, in the form of the bellows wall 18, to expand to its normal extension shown in FIG. 2. This expansion can be achieved by the natural resiliency of the bellows wall 18 or, preferably, the collapsible chamber can contain a resilient means such as a helical compression spring and the like to urge the bellows wall into the extended position shown in FIG. 2.

Referring now to FIG. 3, the check valve means 22 is shown in detail. As there illustrated, the check valve means comprises a raised boss 36 carried on end wall 20 and having a central aperture 38. The boss 36 has an internal retainer 37 which retains a valve member 39 beneath aperture 38, in proximity thereto, whereby positive differential pressure within the collapsible chamber will move the valve member 39 into a sealing engagement against the end wall of boss 36, closing aperture 38.

FIG. 4 illustrates another embodiment of the invention. In this embodiment the container 40 is provided with end walls 41 and 42 distally carried on a rigid external wall 43 which can be of cylindrical, oval or rectangular cross-section. Portion 44 of end wall 42 is attached by hinge means 45 to permit movement of wall portion 44 in the direction of the arrowheaded line. The wall section 46 beneath end wall portion 44 is of flexible construction and overlies an edge portion of wall 43, indicated at 47, for effecting a sealing attachment of the flexible wall 46 to the rigid wall 43. The interior of the rigid wall portion of container 40 is packed with a bed 24 of inert, solid, adsorbent granules such as 26 previously described with reference to FIGS. 1-3. The rigid wall 43 has vapor outlet port means in the form of aperture 49 which has a suitable screen or other foraminous member such as 32, previously described.

The upper surface of end wall portion 44 preferably bears a loop means 50 for receiving a finger or thumb 51 of a user grasping container 40 with the user's hand 52. In this manner the collapsible chamber can be collapsed and extended whereby air can be forced into and out of the bed 24 of solid adsorbent. If desired, the bed 24 can be subdivided by one or more internal baffles 53 to distribute the air flow through the bed in a desirable manner.

The embodiment of FIG. 4 illustrates the invention in the simplest construction whereby the air pump of the collapsible chamber pumps air into and out of the rigid chamber container bed 24 through the vapor port means 49. If desired, forced air circulation throughout the bed 24 of solid granules can be insured by providing a check valve means, such as element 22 described with reference to FIG. 3 in the end wall portion 44.

Referring now to FIG. 5, the embodiment of the invention comprises a container 55 which has an upper internal chamber 56 formed by rigid side wall 57. A bed 24 of inert solid adsorbent granules 26 is contained within this chamber 56 and can be retained between internal, foraminous end walls 58 and 59. The lower edge of the rigid wall 57 is attached to a collapsible wall 60 of bellows construction which overlaps the received end of rigid wall 57 to provide a band 61 that is sealably secured to the rigid wall 57. The opposite end of the bellows collapsible wall 60 has a similar band 62 that receives and is sealably secured to the annular shoulder of a base 63. Base 63 has an end wall, not shown which is provided with check valve means 22, previously described. Preferably, the collapsible chamber defined by the bellows side wall 60 contains a resilient means in the form of a helical coil spring 64 which urges the chamber into the extended position as shown in FIG. 5.

The package of FIG. 5 is used by placing one's hand 65 on the container and urging the container downwardly in the direction indicated by the arrowheaded line. This action will force air through the foraminous end plate 59 and through bed 26, to exit from chamber 56 through apertures 30, dispensing into the atmosphere a controlled amount of volatile deodorant composition.

Referring now FIG. 6, the invention is in the form of a container 70 which can be cylindrical in shape on which is mounted a dispenser hood 71 having an outlet 72 for directing discharged vapors and a base 73 which snaps about the upper rim 74 of container 70. Wall 70 has a large diameter aperture 75 which receives a bulbous flexible membrane 76 that is sealably secured thereto. The bulbous membrane 76 defines the collapsible chamber of the device and, preferably, is provided with check valve means 77 preferably in the form of an integral, internally carried flap which overlies the aperture of the check valve means 77 thereby permitting inflow of air into the flexible chamber but preventing the forced outflow of air therefrom.

The container 70 bears an internal container 78 that defines a rigid wall chamber 79 which receives a bed 24 of inert solid adsorbent granules 26, previously described. The container 78 is of lesser diameter than the internal diameter of outer shell 70 to provide an annular space 80 therebetween. The annular space is in open communication with the flexible chamber defined by the bulbous flexible diaphragm 76.

The base of internal container 78 has a plurality of apertures 81 which communicate into the anular chamber 80. The bed 24 of inert solid granules is carried on a foraminous end wall 82, thereby permitting forced air circulation by the pump means of flexible diaphragm 76 through apertures 81, and foraminous wall 82 to exit through an aperture not shown, in end wall 83 of the outer container 70.

The embodiment shown in FIG. 7 is of substantially the same construction as that of FIG. 6 and includes a deflector hood 72 that is surmounted on container 86. The lower end of container 86 is received within an upright-walled, flexible container 88 having a neck 89 about an intermediate portion of container 86 that is sealingly secured thereto by a band 90. The wall of the flexible container 88 contains a check valve means 77, such as previously described, to permit entrance of air into the internal chamber of container 88. The lower end of container 86 can be provided with plurality of vapor inlet apertures such as 81, previously described while the opposite end is provided with an aperture for discharge of an air stream bearing the volatile constituents.

The bed 24 of solid adsorbent 26 contains a deodorant product of a volatile perfume or masking agent which is adsorbed onto the inert solid particulate carrier. The solid extends the useful life of the deodorant and provides a substantially constant evaporation surface for the perfume agent throughout the life of the product.

The deodorant product comprises a composition of a plurality of volatile ingredients of distinctly different vapor pressures. The volatile ingredients are adsorbed onto an inert solid adsorbent with preselection of one or more of the following: specific surface area, particle size, adsorption isotherm characteristic, or loading (concentration of adsorbate on the solid) to obtain a plurality of component-bearing, solid fractions. The solid fractions are blended together in preselected proportions to provide a proportional release rate of each of the volatile adsorbates which produces the desired vapor composition; and the resultant blend is packaged into a volatile releasing form, such as in a container with a removable seal or closure member. In the preferred method one selects different sizes of a solid carrier which are loaded to saturation or near saturation with respective volatile agents and the resultant solid fractions are blended together in the proper proportions to obtain the desired release rate of each volatile agent.

The volatile product, of one or a plurality of volatile components can be provided as a series of packaged products of the same overall container size and shape and net weight but with distinctly different rates of release of the volatile agent. This permits the product to be packaged and marketed as a series of different volatilities in identical containers. The difference in volatilities are imparted by selection of spherical or substantially spherical (spheroidal) inert particles of different size ranges to provide varied evaporation surface area to each of the product series without any substantial change in the bulk or net weights of the product.

The deodorant composition may include a perfume agent which can be a blend of a plurality of odorous materials. The ingredients of the composition are each adsorbed onto a solid, particulate adsorbent to provide a preselected and controlled proportional release rate of each of the substances during the life of the deodorant composition to maintain throughout such life a constant relationship among the ingredients in the vapor phase.

The perfumes which can be employed can be of flower oils such as obtained by distillation or solvent extraction of cultivated flowers; essential oils usually obtained by steam distillation of plant materials such as leaves, fruits, roots, etc.; animal substances such as extracts of civit, ambergris, musk, etc.; or resinoids, balsams, etc. Synthetic odorous materials can also be employed.

The flower oil which can be used will generally be employed in small proportions to give the deodorant a pleasing odor and temper the harshness of materials such as essential oils, resinoids and the like. The most common flower oils are rose and jasmine, however, other flower oils such as violet, bitter orange tree, mimosa, tuberose, etc. can also be employed.

The essential oils, which are obtained usually by steam distillation of plant materials and which can be used in the invention include lavender, sandalwood, rosewood, citronella, geranium, vetivert, oak moss, bergamot, orris, citrous oils, etc.

Concentrates of the essential oils usually obtained by distillation or extraction are available under the designation of isolates. Of these, materials such as citronellol, geraniol, citral, can be used. Various synthetic materials having similar odorous characteristics to these materials are also available.

The animal origin materials are usually employed in relatively minor quantities to empart a lasting quality to the deodorant, often exhibiting a synergistic affect on the odor of the perfumes. Examples of these are extracts of musk, civet, ambergris, castoreum, etc.

The resinoids which can be employed include myrrh, styrax, benzoin, olibanum, galbanum, etc.

Typically the deodorant employs a relatively low concentration of the perfume substance; from one to about twenty weight percent, usually from two to about ten percent. The balance of the deodorant composition comprises a solvent or liquid carrier such as alcohol, e.g., isopropanol, ethanol, butanol, isobutanol, etc. Other solvents which can be employed alone or in combination with any of the foregoing substances include the glycols such as propylene glycol, ethylene glycol, etc.

Any of a wide variety of finely subdivided solids can be used as the solid adsorbent for the volatile ingredients. Typical of these materials are titania, zirconia, alumina, silica, etc., or combination of these materials. Examples include silica, Fuller's earth, diatomaceous earth, calcium or sodium silicates, expanded calcium silicate (pearlite), expanded sodium silicate, alumina, silica stabilized alumina containing from 1 to 15 percent silica as described in U.S. Pat. No. 2,437,532, the aluminum silicates, clay, naturally occurring or synthetically prepared zeolites such as chabazite, gnelenite or faujasite, as well as synthetic zeolites. The latter materials are partially dehydrated crystalline compositions of silica and alumina and contain quantities of 1 or more exchangeable cations such as sodium, potassium, hydrogen, magnesium, calcium, etc. The compositions and their preparation are described in U.S. Pat. Nos. 2,882,243 and 2,882,244. These compositions are characterized by crystal pores of relatively uniform pore diameter between about 5 and 14 Angstrom units. Several crystal forms of such molecular sieves are available and suitable for use herein as the carrier for the volatile perfume agents of my invention including the X, Y, L and J crystal types. Other materials which can be used include botanical flours such as soybean flour, wheat flour, tobacco flour, cottonseed flour walnut shell flour, wood flour, sawdust, etc. Other materials that can be used include particulate solid metal carbonates and sulphates. Examples of suitable carbonates include calcite and dolomite. A suitable sulfate is gypsum.

The size range of the particles can be widely varied to provide the desired control over the volatile release rate. Typically, solids having a particle diameter of one inch and less and retained on about a number 120, U.S. Standard size sieve can be used, corresponding in particle diameters from 1.0 inch to about 0.005 inch. Preferably, the size range of solids is from number 3 to about number 16 size sieve, corresponding to particle diameters from about 0.25 to 0.05 inch. The use of more finely subdivided particles is not desirable since such particles significantly reduce ventilation and air circulation through the product, resulting in an undesirably low rate of release of volatile agent.

When the size range of the solid adsorbent is used to control the release rate of a volatile component or agent, the solid particles are preferably of a medium to narrow size range, e.g., solid fractions passing and retained on screens differing by about 1 to 5 numbers, preferably 1 to about 3 numbers, on the aforementioned U.S. Standard screen size scale.

The characteristic of volatile materials adsorbed on an inert solid adsorbent can be conveniently depicted by an adsorption isotherm which is a plot of the adsorbate vapor pressure against its volume adsorbed on a constant amount of adsorbent. For inert solid adsorption, the mechanism is physical adsorption which consists of monolayers, multilayers and/or condensation of the adsorbate as a liquid in the capillaries of the adsorbent. Physical adsorption phenomenon is generally accepted to result from physical or Van der Walls forces between the adsorbate and the solid adsorbent.

Figure 9:
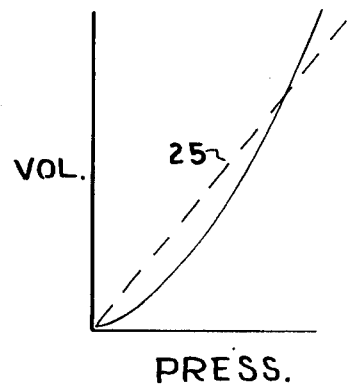
Figure 10:
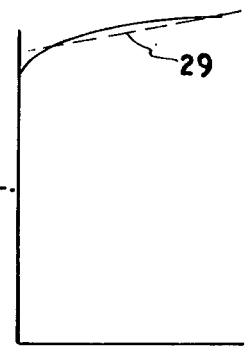

FIGS. 8-10 illustrate typical adsorption isotherms. The isotherm illustrated in FIG. 8 is characteristic of adsorption of a vapor as thick multilayers of the adsorbate on the surface of the adsorbent. FIG. 9 illustrates a typical isotherm which is characteristic of the adsorption of a gas or vapor on a solid in which the heat of adsorption is less than the heat of liquification of the vapor. FIG. 10 illustrates another adsorption phenomenon representative of the adsorption of a vapor on a solid adsorbent in monomolecular film thicknesses.

FIGS. 8-10 thus illustrate that the vapor pressure of an adsorbate decreases along a predictable and known relationship as the concentration of the adsorbate on the solid adsorbent decreases. This relationship can be approximated by an average, straight-line relationship as shown by the broken lines 27, 25 and 29 for each of FIGS. 8, 9 and 10. To provide a substantially constant release rate of a volatile deodorant throughout its life, a combination of solid adsorbent and volatile agents having an adsorption isotherm comparable to that of FIG. 10 can be selected.

Figure 11:
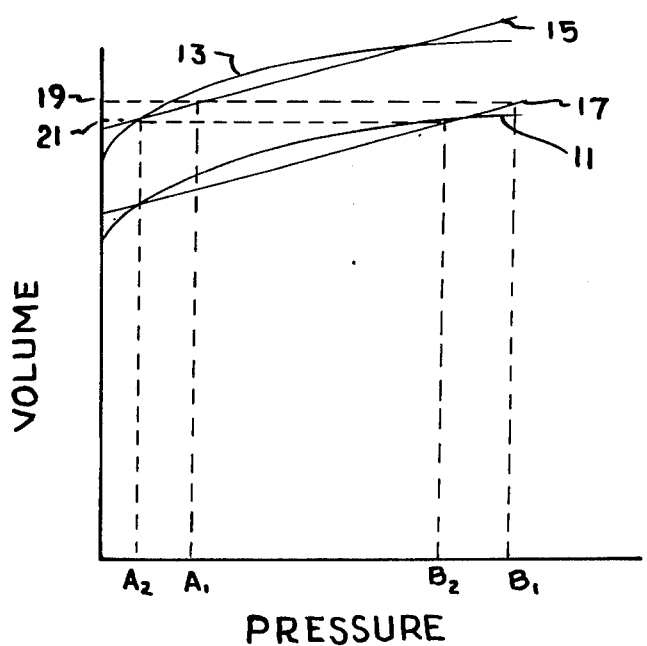
FIG. 11 illustrates the adsorption isotherms of a mixture of two volatile-containing solid fractions.

The invention is practiced by providing the combination of solid adsorbent and vapor, or volatile perfume agent, that will provide approximately matching adsorption isotherm characteristics. This is illustrated in FIG. 11 in which the adsorption isotherm of a physical blend of volatile component A bearing solid fraction and volatile component B bearing solid fraction are blended together. The adsorption isotherm of the solid fraction bearing volatile component A is shown by the curved line 13 while that of the solid fraction bearing volatile component B is illustrated by the curved line 11. These volatile components A and B are adsorbed onto adsorbents which provide the adsorption isotherms of the same general configuration, typically that shown in FIG. 11. This type of adsorption is generally exhibited by non-polar volatile components which are adsorbed on a solid adsorbent such as charcoal. Accordingly, most of the volatile perfume agents previously described, which are non-polar compounds, can be convenient adsorbed on a material such as charcoal to provide solid fractions of adsorption isotherms of approximately the same configuration. The average behavior of the adsorbate of these fractions is depicted by the straight lines 15 and 17 for components A and B, respectively. Since the straight line average characteristic of the adsorbates are substantially parallel, it can be seen that the vapor pressures of the volatile components are in substantially constant proportion, resulting in the release of a vapor of substantially constant concentration of components A and B throughout the life of the composition. This is illustrated by the two points 19 and 21 on the volume concentration scale; line 19 corresponding to the initial or early condition of the deodorant composition when the material has a high proportion of volatile components and point 21 corresponding to a more aged or used composition having a lower total concentration of volatile components.

The invention has been described with illustration of the presently preferred embodiments thereof. It is not intended that the invention be unduly limited by the illustrated and preferred embodiments. Instead, it is intended that the invention be defined by the means and steps, and their obvious equivalents, set forth in the following claims.

What is claimed is:

1. A volatile component dispensing package comprising:
    a. container means having an apertured internal wall subdividing said container into internal, first and second chambers;
    b. a collapsible external wall portion sealingly mounted to, and defining an external wall of said second chamber of, said container;
    c. a single check valve in the external wall of said chamber, directly communicating with said second chamber to permit air intake directly into said second chamber;
    d. a bed of inert solid adsorbent granules within said first chamber;
    e. a volatile ingredient for dispensing into the atmosphere adsorbed on said solid adsorbent granules; and
    f. a vapor outlet port in the external wall of said container directly communicating with said first chamber whereby air can be induced through said single check valve means into said second chamber and forced therefrom through said apertured internal wall to flow through said solid adsorbent and desorb said volatile ingredient and discharge with said volatile ingredient through said outlet port.

2. The package of claim 1 wherein said single check valve comprises an aperture with a flap closure member carried on the inside wall to overlie said aperture.

3. The package of claim 1 wherein said solid adsorbent and volatile ingredient adsorbate provide an adsorption isotherm characteristic of substantially constant vapor pressure as a function of the concentration of said adsorbate.

4. The package of claim 3 wherein said solid adsorbent comprises particulate solids of substantially spherical shape.

5. The package of claim 3 wherein said solid adsorbent is silica.

6. The package of claim 3 wherein said solid adsorbent is charcoal.

7. The package of claim 1 wherein said bed of inert solid adsorbent granules comprises an admixture of a plurality of inert solid fractions, each fraction comprising an inert, particulate solid carrier having adsorbed thereon a volatile ingredient of a volatile-dispensing composition to provide volatile, component-bearing solid fraction of preselected specific surface area, adsorbate concentration, particle size and adsorption isotherm characteristics and admixed with the other solid fractions at a concentration to provide a proportional release rate of its respective volatile component whereby the vapor released from said deodorant product is of a preselected, desired composition.

8. The package of claim 7 wherein said solid fractions have preselected adsorption isotherm characteristics to release a vapor of substantial constant composition throughout the useful life of said product.

9. The package of claim 7 wherein said solid carrier is charcoal.

10. The package of claim 7 wherein said solid carrier is silica.

11. The package of claim 7 wherein said solid carrier is expanded calcium silicate.

12. The package of claim 7 wherein said volatile-dispensing composition is a deodorant.

UNITED STATES PATENT AND TRADEMARK OFFICE
CERTIFICATE OF CORRECTION

PATENT NO. : 4,146,566

DATED : March 27, 1979

INVENTOR(S) : Conrad J. Gaiser

It is certified that error appears in the above—identified patent and that said Letters Patent are hereby corrected as shown below:

Change the address of the inventor from "24 S. 66th Place, Long Beach, Calif. 90803" to --P.O. Box 534, Zephyr Cove, Nevada 89448--.

Signed and Sealed this

Twenty-fifth Day of December 1979

[SEAL]

Attest:

SIDNEY A. DIAMOND

Attesting Officer

Commissioner of Patents and Trademarks